United States Patent
Gruenberg

(10) Patent No.: US 9,901,482 B2
(45) Date of Patent: Feb. 27, 2018

(54) METHOD FOR PRODUCING A PROTRUSION SPLINT

(71) Applicant: HICAT GMBH, Bonn (DE)

(72) Inventor: Daniel Gruenberg, Bonn (DE)

(73) Assignee: HICAT GMBH, Bonn (DE)

( * ) Notice: Subject to any disclaimer, the term of this patent is extended or adjusted under 35 U.S.C. 154(b) by 177 days.

(21) Appl. No.: 14/774,137

(22) PCT Filed: Mar. 11, 2014

(86) PCT No.: PCT/EP2014/054695
§ 371 (c)(1),
(2) Date: Sep. 10, 2015

(87) PCT Pub. No.: WO2014/140007
PCT Pub. Date: Sep. 18, 2014

(65) Prior Publication Data
US 2016/0022472 A1 Jan. 28, 2016

(30) Foreign Application Priority Data
Mar. 12, 2013 (DE) .................. 10 2013 102 473

(51) Int. Cl.
*G05B 19/00* (2006.01)
*A61F 5/56* (2006.01)
*G05B 19/4099* (2006.01)

(52) U.S. Cl.
CPC .......... *A61F 5/566* (2013.01); *G05B 19/4099* (2013.01); *G05B 2219/35134* (2013.01)

(58) Field of Classification Search
CPC ....................................................... A61F 5/56
See application file for complete search history.

(56) References Cited

U.S. PATENT DOCUMENTS 5,462,066 A 10/1995 Snyder
5,921,942 A 7/1999 Remmers et al.
(Continued)

FOREIGN PATENT DOCUMENTS

DE 10 2005 031 233 B3 11/2006
DE 20 2008 011 841 U1 11/2008
(Continued)

OTHER PUBLICATIONS

"Dolphin Imaging—3D", Dolphin Imaging & Management Solutions, a Patterson Technology, www.dolphin.com, pp. 1-40 (2010-2013).

*Primary Examiner* — Vincent Tran
(74) *Attorney, Agent, or Firm* — Norman B. Thot

(57) ABSTRACT

A method for manufacturing a protrusion splint comprising an upper support area configured to provide a defined abutment of a maxilla area, and a lower support area configured to provide a defined abutment of a mandible area. The method includes fixing the maxilla area and the mandible area in a first position so that the mandible area is shifted forward relative to the mandible area. A three-dimensional image data set of an air passage in a region of a trachea is created in the first position. The air passage is checked whether an opening value of the air passage corresponds to a target value. A second position of the maxilla area and of the mandible area to each other is defined depending on the checking. The protrusion splint is manufactured so that the mandible area is held relative to the maxilla area in the second position.

12 Claims, 4 Drawing Sheets

(56) References Cited

U.S. PATENT DOCUMENTS

| | | |
|---|---|---|
| 2005/0175954 A1 | 8/2005 | Zacher |
| 2005/0241646 A1 | 11/2005 | Sotos et al. |
| 2007/0183572 A1 | 8/2007 | Drummond et al. |
| 2007/0209666 A1 | 9/2007 | Halstrom et al. |
| 2007/0235037 A1 | 10/2007 | Thornton |
| 2007/0255161 A1* | 11/2007 | De Backer ........ A61M 16/0006 600/532 |
| 2008/0064008 A1* | 3/2008 | Schmitt .............. A61C 13/0004 433/140 |
| 2009/0090371 A1* | 4/2009 | Toussaint ................ A61F 5/566 128/848 |
| 2010/0316973 A1 | 12/2010 | Remmers et al. |
| 2011/0155144 A1 | 6/2011 | Tousssaint |
| 2011/0178439 A1* | 7/2011 | Irwin ...................... A61F 5/566 600/590 |
| 2014/0370465 A1* | 12/2014 | Lucas ...................... A61C 7/36 433/214 |

FOREIGN PATENT DOCUMENTS

| | | |
|---|---|---|
| DE | 10 2009 009 916 A1 | 9/2010 |
| EP | 1 203 570 B1 | 3/2006 |
| GB | 2 389 796 A | 12/2003 |
| JP | 2012-528698 A | 11/2012 |
| WO | WO 2012/172112 A1 | 12/2012 |

* cited by examiner

B)

A)

B)

A)

METHOD FOR PRODUCING A PROTRUSION SPLINT

CROSS REFERENCE TO PRIOR APPLICATIONS

This application is a U.S. National Phase application under 35 U.S.C. § 371 of International Application No. PCT/EP2014/054695, filed on Mar. 11, 2014 and which claims benefit to German Patent Application No. 10 2013 102 473.4, filed on Mar. 12, 2013. The International Application was published in German on Sep. 18, 2014 as WO 2014/140007 A1 under PCT Article 21(2).

FIELD

The present invention relates to a method for manufacturing a protrusion splint.

BACKGROUND

Protrusion splints to treat snoring have previously been described. The prior art describes removable teeth splints which are, for example, made of plastic, which are similar to the orthodontic appliances, or so-called scrunching splints. The removable teeth splints are worn in the mouth during sleep and affect the mandible position, the tongue position, and other soft tissues. These body parts are here kept in a forward position (=protrusion) as described in U.S. Pat. No. 5,462,066 and EP 1 203 570 B1. A falling back of the lower jaw and the attaching soft parts is thereby prevented, especially in the supine position of the patient. This results in an increase of the throat area with a clear airway respiratory duct during sleep and a healthy night time breathing without interruption in breathing and without snoring.

The previously-described methods to manufacture protrusion splints mainly use empirical data that have been verified by experiments in the sleep laboratory to adjust the position of the protrusion. At first setup of an allegedly suitable position occurs. The patient must then spend one or more nights with the inserted protrusion splint in the sleep laboratory to check whether the treatment with the accordingly set protrusion splint delivers the desired results. These experiments are, however, complex and less then comfortable for the patient. It has furthermore been determined that the long-term use of the protrusion splint may adversely affect the temporomandibular joints. By charging the jaws in the position predetermined by the splint, the temporomandibular joints can thus be brought into a condition which is unnatural, and which can damage the temporomandibular joints. This results in the treatment not generally being carried out with protrusion splints for those patients having troubles with their temporomandibular joints.

SUMMARY

An aspect of the present invention is to provide an improved method for manufacturing a protrusion splint.

In an embodiment, the present invention provides a method for manufacturing a protrusion splint comprising an upper support area configured to provide a defined abutment of a maxilla area, and a lower support area configured to provide a defined abutment of a mandible area, wherein, during the respective defined abutments, the mandible area is held relative to the maxilla area in a position specified by the protrusion splint. The method includes fixing the maxilla area and the mandible area in a first position so that the mandible area is shifted forward relative to the mandible area when compared to a normal position of a jaw. A three-dimensional image data set of an air passage in a region of a trachea is created while the maxilla area and the mandible area are fixed in the first position. The air passage is checked based on the three-dimensional image data set whether, in the first position, an opening value of the air passage corresponds to a target value. A second position of the maxilla area and of the mandible area to each other is defined depending on a result of the checking of the air passage. The protrusion splint is manufactured so that, during the respective defined abutments, the mandible area is held relative to the maxilla area in the second position.

BRIEF DESCRIPTION OF THE DRAWINGS

The present invention is described in greater detail below on the basis of embodiments and of the drawings in which.

DETAILED DESCRIPTION

Figure 1:
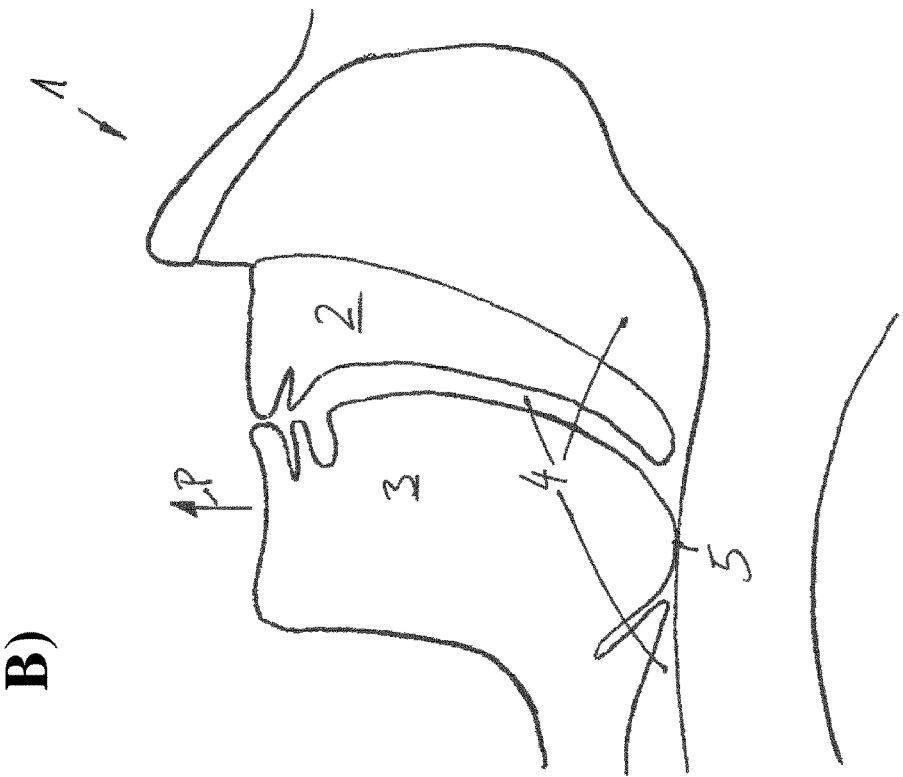
FIG. 1 shows a cross section of a cranium where A) shows a low risk of snoring, and B) shows an increased risk of snoring.
Figure 1:
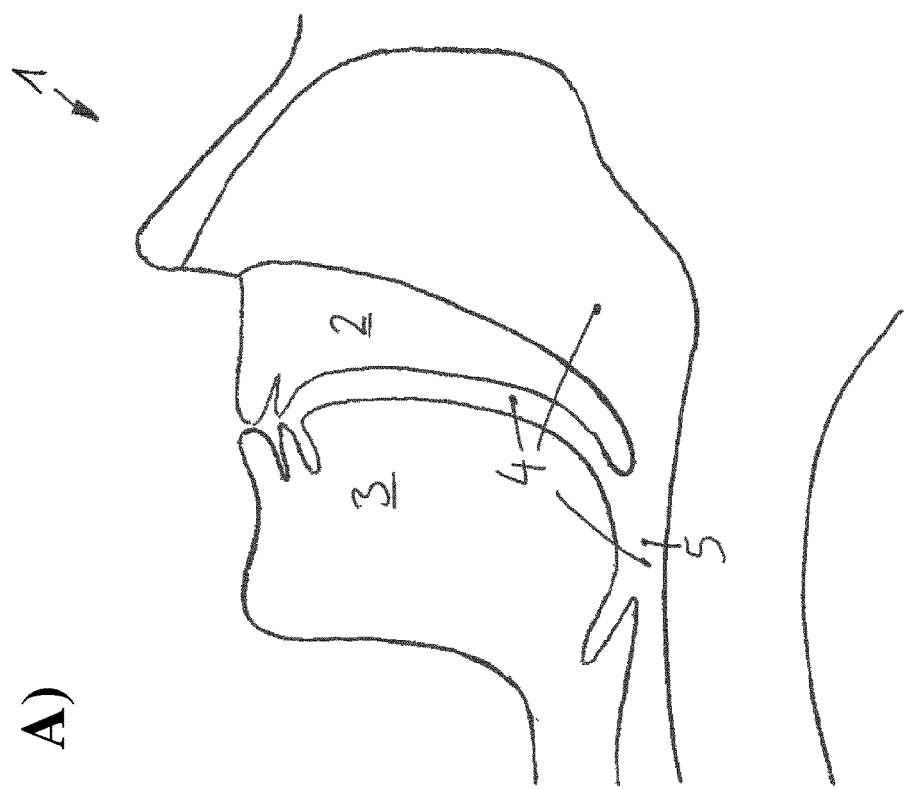

The essence of the present invention is, in particular, that to check the first position, knowledge is used which was obtained using a three-dimensional image data set. The image data set is created especially with a tomographic imaging method. The jaw is held in the first position, in particular by an adjustable protrusion splint. The first position is a position at which the jaw position is shifted out from its normal position so that the mandible is displaced forwardly (anterior) in relation to the normal position. The first position may already represent the second position if the result is that a successful treatment is provided thereby and in particular no damage to the temporomandibular joints is generated. In the first position, it is therefore initially checked whether the corresponding air passage was enlarged so that a reduction of snoring is expected. The three-dimensional image data set can therefore be evaluated so that an opening value of the air passage is determined. Such an opening value may, for example, be the smallest cross-section of the trachea during the first position; however, it may also be the total volume of a portion of the trachea in the area of trachea to be observed, which can correspond to an integration of individual opening cross-sections along the length of the observed trachea section. The shape of the air passage can in principle also be checked as can a distance of two opposite walls of the trachea to each other.

Based on the determined opening value, it can be detected if the adopted first position is suitable to provide a successful treatment. To this end, a comparison of the determined opening value with a target value can, for example, be performed. The target value may be a value or range of values in which the opening value must lie.

If the opening value corresponds to the target value, it is defined that the first position is at the same time the second position. In case it is determined that the opening value does not correspond to the target value, another second position is determined. For the latter case, the second position may also be calculated from a difference between the determined opening value and the target value. For this purpose, a correction value can be determined, via which the second position is calculated from the first position. The correction value may thus, for example, be a feed value by which the mandible is shifted relatively out of the first position so that it reaches a suitable second position. Such a correction value can, for example, be derived from historical test data from which is, for example, known that a feed to the value of X or X % results in an increase of the opening value to the value of Y or y %. Such a calculative procedure can be performed if, for example, the difference between the measured opening value and the target value is quite low, especially since recreating the expensive three-dimensional image data set is avoided. A modified first position is otherwise adopted. A three-dimensional image data set of the air passage is then again created. The opening size of the air passage in the amended first position is determined therefrom, and it is again decided whether the amended first position is to be defined as the second position. This process can be repeated as often as desired.

In an embodiment of the present invention, a bite registration can, for example, be used to manufacture the protrusion splint. The patient thereby bites on the bite registration while the patient's jaws are in one of the positions. The patient leaves impressions of some teeth of the maxilla and the mandible, which are mutually aligned according to the position. Impressions or scans of the two jaws, which were made in an arbitrary position, can then be aligned to each other on the basis of the bite registration according to the adopted position. In case the orientations of the two impressions or scans of the jaws are known, the protrusion splint device can be prepared, as described, for example, in DE 10 2009 009 916 A1.

In an embodiment of the present invention, for creating the three-dimensional image data set, surface data can, for example, be superimposed with an optical data scan of the jaw areas. Dental negatives are calculated therefrom, on the basis of which the protrusion splint is manufactured. Surface values, which are extracted solely from the three-dimensional image data set, are usually not accurate enough so that such data can solely be used to manufacture the protrusion splint. From the three-dimensional image data set, the relative position of individual teeth to each other can, however, be determined very well. If the very good position data of the three-dimensional image data are linked to the very good surface data of the optical scans, a very precise protrusion splint can be manufactured without requiring an impression.

The described method allows the best possible position to be determined as exactly as possible. This is particularly advantageous since a position in which the mandible is shifted too far forward relative to the normal position can create problems in the temporomandibular joints. It is thus desirable to shift the mandible forward as far as necessary, but as little as possible.

In order to additionally avoid problems of the temporomandibular joints, the condition of the temporomandibular joints can, for example, be investigated in the second position or in the first position. A three-dimensional image data set of the temporomandibular joints is created for this purpose. This three-dimensional image data set can, for example, be created together with the three-dimensional image data set of the air passage in the first position. Based on this image data of the temporomandibular joints, it can then be determined whether problems in the temporomandibular joints can be caused by shifting into the position. If applicable, the protrusion splint can then be optimized to avoid the problems of the temporomandibular joints to the extent possible. It can be determined even for persons who already suffer from temporomandibular joint problems whether the position adversely affects the existing temporomandibular joint problems. If this is not the case, the process of the present invention provides that even people suffering from temporomandibular joints problems can use the protrusion splints to treat snoring and it is not per se a priori excluded.

Such a protrusion splint is particularly suitable to treat disturbing, non insanitary snoring. The splints are also suitable for other applications, in particular to treat sleep apnea.

The present invention is subsequently explained in greater detail under reference to the drawings.

FIG. 1 shows two cross-sectional views of a human cranium. The illustration in A) of FIG. 1 shows a cranium 1 with little risk of snoring. On the cranium 1, the maxilla 2 and mandible 3 can be seen. Respiratory ducts 4 in the area of the mouth, the nose, and the trachea are drawn. In the area of a trachea, an air passage 5 can be seen, which is formed sufficiently large to allow a sufficient air flow into the lung and out of the lung during sleep. In the illustration of B) in FIG. 1, which shows the cross section of the human cranium 1 with an increased risk of snoring, the air passage 5 is significantly reduced compared to the condition in A) of FIG. 1. The risk of snoring is often caused by a relaxation of musculature in the area of the respiratory ducts 4. A commonly used option to treat snoring is the displacement of the mandible 3 into a protruded position compared to the maxilla 2, which is indicated in B) of FIG. 1 by arrow P. Compared to the normal position of the maxilla 2 and mandible 3, as shown in A) and B) of FIG. 1, the mandible 3 is brought into a position relative to the maxilla 2 in which the mandible 3 is shifted in a forward direction, anterior, (see also below in B) of FIG. 3). For this purpose, a protrusion splint 6 is used, as it is schematically shown in FIG. 2.

The protrusion splint 6 has an upper support area 7, which comprises a plurality of dental negatives 9 of the maxilla. The protrusion splint 6 likewise has a lower support area 8 having a plurality of dental negatives 10 of the mandible. The upper and lower dental negatives 9, 10 are produced by a machine using a plaster cast or by using a digital scan. The patient can now bite with his/her maxilla 2 into the upper support area 7 and with the mandible 3 into the lower support area 8. When the teeth of the maxilla 2 and of the mandible 3 abut against the dental negatives 9, 10, the mandible 2 compared to the maxilla 3 is then held in this position, which is defined by the protrusion splint 6. Within the scope of the present invention, the teeth are understood as being a part of the jaws or jaw areas.

Figure 3:
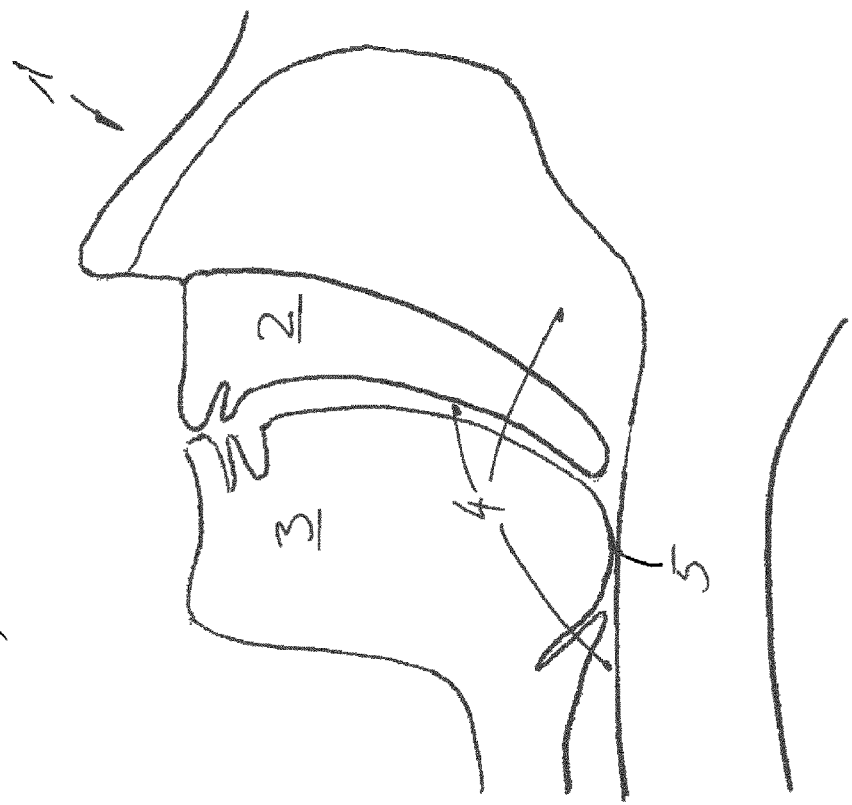
FIG. 3 shows a cross-section of a cranium with an increased risk of snoring where A) shows the cranium with an inserted protrusion splint, and B) shows the cranium without an inserted protrusion splint.
Figure 3:
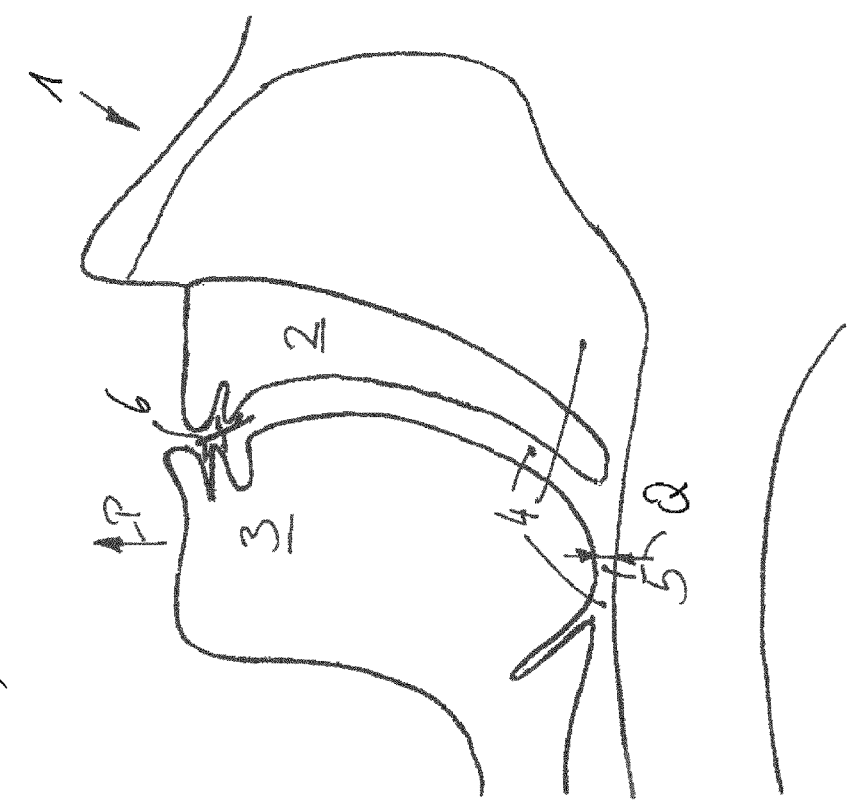

This position is also visualized in FIG. 3. A) of FIG. 3 shows the protrusion splint 6, which now abuts with the maxilla area 2 and the mandible 3. It can be seen that the mandible 3 is moved forward compared to the normal position (B) of FIG. 3 according to arrow P. The effect is achieved that via the "shifting forward", the cross-section Q of the air passage 5 is larger than in the normal state according to B) of FIG. 3. The patient can now again breathe well and has a peaceful sleep.

Figure 2:
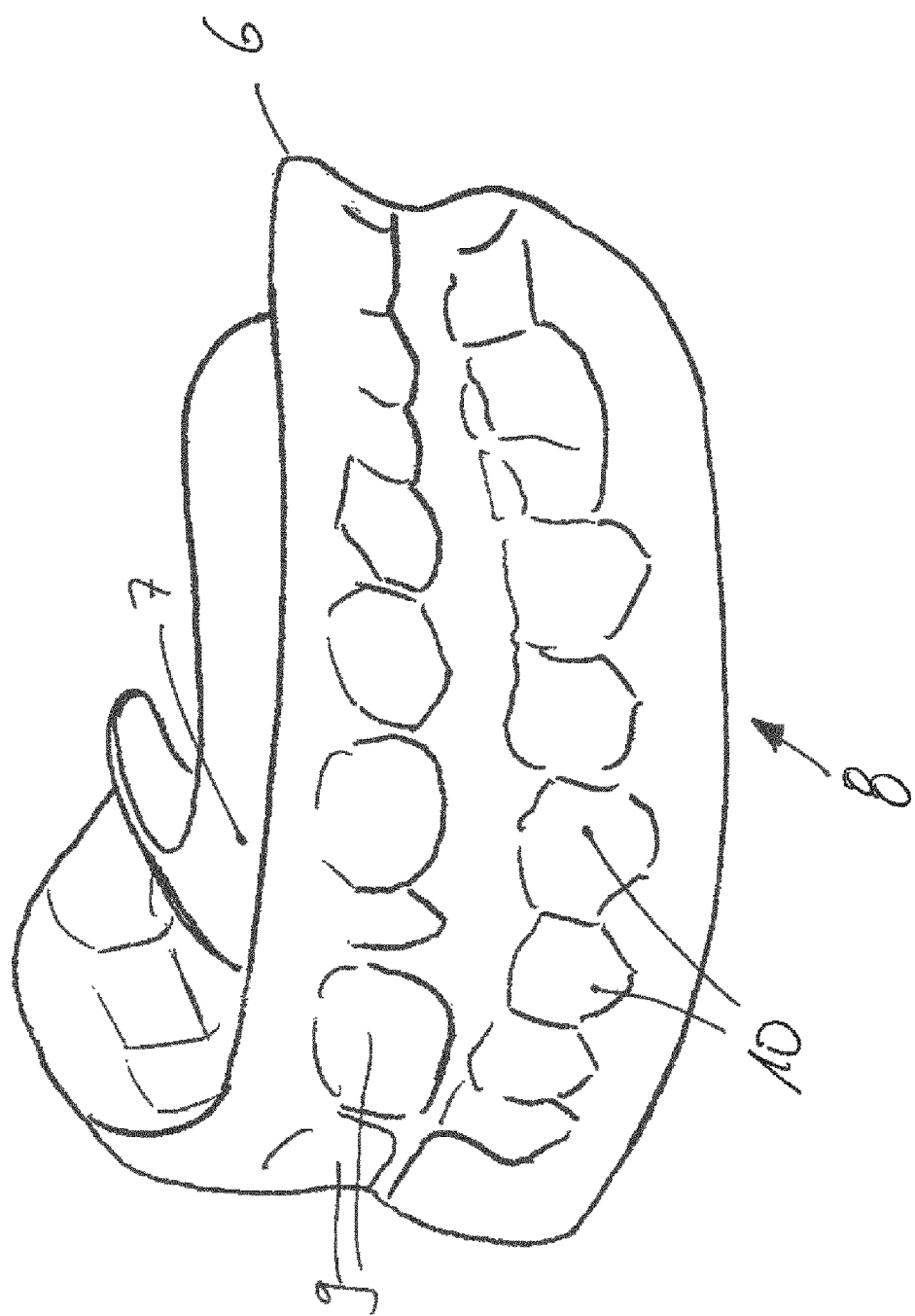
FIG. 2 shows a protrusion splint manufactured according to the present invention.

Before manufacturing the protrusion splint 6 according to FIG. 2, the maxilla 2 and mandible 3 are aligned to each other in a first position, which is a similar or even an identical situation as shown in A) of FIG. 3. The trachea area is then subjected to a three-dimensional tomographic imaging method to create a three-dimensional image data set, by which detailed knowledge of the spatial conditions in the air passage 5 is provided.

Figure 4:
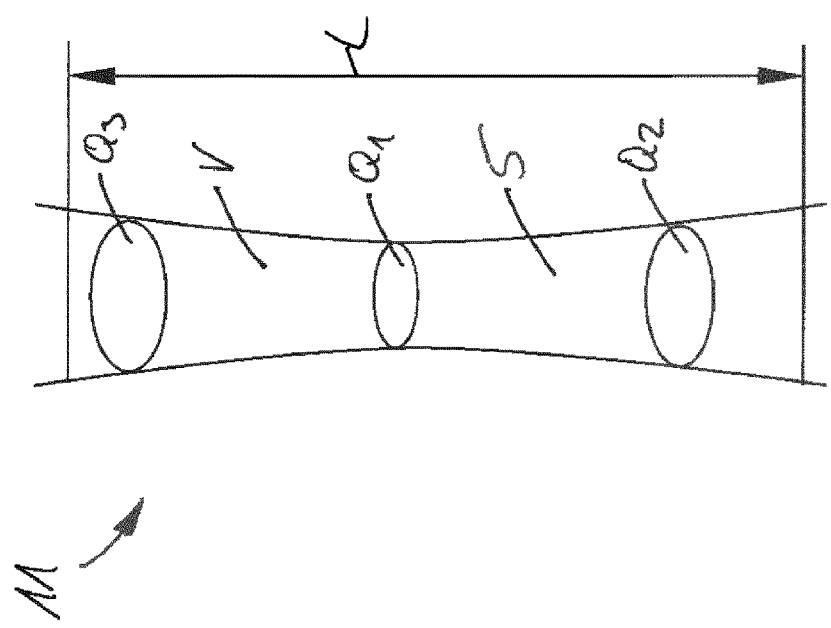
FIG. 4 schematically shows a tomographic image of the trachea region.

FIG. 4 shows a created three-dimensional representation 11 of the air passage 5. With the help of these three-dimensional representations 11, the cross-sectional areas $Q_1$, $Q_2$, $Q_3$ of the air passage 5 can be calculated at different positions of the air passage 5. Software that performs such calculations is available under the name "Dolphin Imaging 3D". The cross-section $Q_1$ is, for example, the smallest cross-section in the air passage 5. The smallest cross-sectional value $Q_1$ can be a significant opening value for assessing whether the air passage 5 is sufficient for treatment. This smallest cross-sectional value $Q_1$ is then compared with a target value. If the cross-sectional value $Q_1$ is greater than the target value, the first position is suitable to keep the air passage in a respective dimension so that the risk of snoring can be eliminated. The first position is then set as the second position. If the value $Q_1$ is, however, smaller than the target value, it is determined that the first position is not suitable to eliminate the risk of snoring. A new position must then be determined, which may be verified by the same steps.

A too large cross-section $Q_1$ may, however, provide insight that the first position is not optimal. This is because a too large move forward (protrusion) may also produce a quite unnatural position which is too far removed from the normal position. Damage to the temporomandibular joints may result therefrom. It is therefore advantageous if, in addition to the investigations of the air passage, an investigation of the temporomandibular joints also takes place. A recording of the temporomandibular joints is therefore created at the same time in the previously mentioned imaging process. If it the result is that the condition of the temporomandibular joint can cause damage to the temporomandibular joints, the position can be changed.

Other dimensions, that can be determined by the three-dimensional representation, can also be used to verify the first position. By integrating the individual cross sections $Q_1$, $Q_2$, $Q_3$ over a total length L of the air passage 5, a total volume V of the air passage 5 can be determined. This can also be the relevant cross-sectional dimension of the method and can be compared to a corresponding target value.

Figure 5:
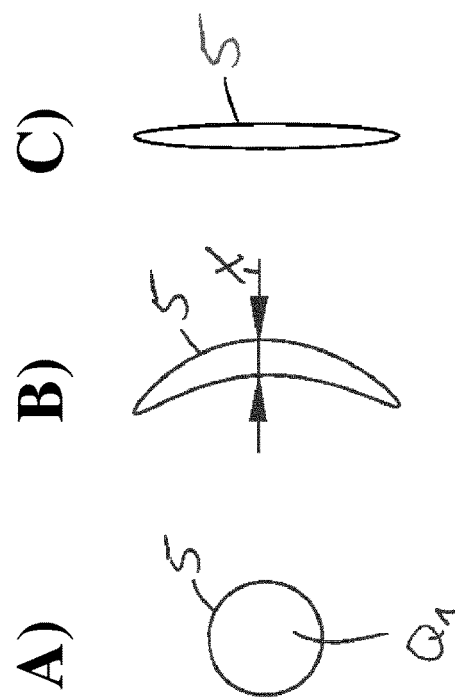
FIG. 5 schematically shows different cross sections of the trachea region in a top view with the jaw positioned A) in a suitable position, B) in an unsuitable position, and C) in a normal position.

FIG. 5 shows other possible cross-sections. A) of FIG. 5 shows a circular cross-section $Q_1$ corresponding to FIG. 4, which indicates a suitable position. A kind of U-shaped cross-sectional area $Q_4$ is shown in B) of FIG. 5. Although the dimension of the cross-sectional area may be sufficient for a successful treatment, the shape of the cross-sectional area is, however, unfavorable since a distance X between two opposite walls of the air passage is too small. The distance X therefore also presents a relevant opening value.

An adjustable protrusion splint can be used to fix the maxilla 2 and mandible 3 in the first position. This comprises separate upper and lower support areas which can be brought into different positions to each other and can be fixed therein. If the patient then wears this adjustable protrusion splint, the three-dimensional image data set is created. The bite registration is also made while the patient wears the adjustable protrusion splint. An adjustable protrusion splint is described in DE 20 2008 01 1841 U1.

The protrusion splint manufactured in this way can also be used to treat sleep apnea.

The present invention is not limited to embodiments described herein; reference should be had to the appended claims.

LIST OF REFERENCE NUMBERS 1. cranium
2. maxilla
3. mandible
4. respiratory ducts
5. air passage
6. protrusion splint
7. upper support area
8. lower support area
9. dental negative (maxilla)
10. dental negative (mandible)
11. three-dimensional representation
Q cross-sectional area of air passage
L length of the air passage
V volume of the air passage
X distance between two opposing walls of the air passage

What is claimed is:

1. A method for manufacturing a protrusion splint, the protrusion splint comprising:
   an upper support area configured to provide a defined abutment of a maxilla area; and
   a lower support area configured to provide a defined abutment of a mandible area;
   wherein, during the respective defined abutments, the mandible area is held relative to the maxilla area in a position specified by the protrusion splint,
the method comprising:
   fixing the maxilla area and the mandible area in a first position with an adjustable protrusion splint so that the mandible area is shifted forward relative to the maxilla area when compared to a normal position of a jaw;
   creating a three-dimensional image data set of an air passage in a region of a trachea while the maxilla area and the mandible area are fixed in the first position;
   checking the air passage based on the three-dimensional image data set whether, in the first position, an opening value of the air passage corresponds to a target value;
   defining a second position of the maxilla area and of the mandible area to each other depending on a result of the checking of the air passage; and
   manufacturing the protrusion splint so that, during the respective defined abutments, the mandible area is held relative to the maxilla area in the second position.

2. The method as recited in claim 1, wherein, during the checking of the air passage based on the three-dimensional image data set whether, in the first position, the opening value of the air passage corresponds to the target value, the method further comprises:
   determining the air passage; and
   comparing the air passage with the target value.

3. The method as recited in claim 2, wherein, if the opening value does not correspond to the target value, the method further comprises:
   determining a correction value based on a difference between the opening value and the target value; and
   setting the second position from the first position,
   wherein, a three-dimensional image data set of the air passage is not again created.

4. The method as recited in claim 1, wherein, if the opening value does not correspond to the target value, the method further comprises:
   repeating the fixing step, the creating step, and the checking step as recited in claim 1 in a modified first position prior to the defining step and the manufacturing step.

5. The method as recited in claim 1, wherein the opening value is,
   a cross-sectional area of the air passage,
   a volume of the air passage, or
   a distance between two opposing walls of the air passage.

6. The method as recited in claim 1, wherein, when manufacturing the protrusion splint, the method further comprises:
   determining a relative orientation of at least one tooth of the maxilla area to at least one tooth of the mandible area in the second position;
   producing a three-dimensional dental negative of the mandible area and a three-dimensional dental negative of the maxilla area based on an image of the maxilla area and on an image of the mandible area; and
   arranging the three-dimensional dental negative of the mandible area and the three-dimensional dental negative of the maxilla area to one another in the protrusion splint according to a relative orientation in the second position.

7. The method as recited in claim 6, wherein the determining of the relative orientation is performed via a bite registrate.

8. The method as recited in claim 1, wherein, for creating the three-dimensional image data set, the method further comprises:
   superimposing the three dimensional image data set with surface data of an optical scan of the maxilla area and of the mandible area;
   producing a three-dimensional dental negative of the mandible area and a three-dimensional dental negative of the maxilla area; and
   manufacturing the protrusion splint based the three-dimensional dental negative of the mandible area and the three-dimensional dental negative of the maxilla area.

9. The method as recited in claim 1, further comprising:
   performing an investigation of a condition of the temporomandibular joints in at least one of the second positing and in the first position.

10. The method as recited in claim 9, wherein, when creating the three-dimensional image data set, three-dimensional image data of the temporomandibular joints are created in addition to the three-dimensional image data of the air passage.

11. A protrusion splint manufactured by the method as recited in claim 1.

12. A method of using a protrusion splint manufactured by the method as recited in claim 1 to treat disruptive snoring, the method comprising:
   providing a protrusion splint manufactured by the method as recited in claim 1; and
   inserting the protrusion splint into the jaw of a patient so as to treat disruptive snoring.

* * * * *